United States Patent
Heinrich et al.

(10) Patent No.: US 10,136,853 B2
(45) Date of Patent: Nov. 27, 2018

(54) CONTACTLESS SLEEP DISORDER SCREENING SYSTEM

(75) Inventors: Adrienne Heinrich, Den Bosch (NL); Roy Joan Eli Marie Raymann, Waalre (NL); Henriette Christine Van Vugt, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 355 days.

(21) Appl. No.: 14/008,016

(22) PCT Filed: Mar. 28, 2012

(86) PCT No.: PCT/IB2012/051474
§ 371 (c)(1),
(2), (4) Date: Oct. 31, 2013

(87) PCT Pub. No.: WO2012/131589
PCT Pub. Date: Oct. 4, 2012

(65) Prior Publication Data
US 2014/0046184 A1    Feb. 13, 2014

Related U.S. Application Data
(60) Provisional application No. 61/469,329, filed on Mar. 30, 2011.

(51) Int. Cl.
*A61B 5/00* (2006.01)
*A61B 5/11* (2006.01)
(Continued)

(52) U.S. Cl.
CPC .......... *A61B 5/4806* (2013.01); *A61B 5/0059* (2013.01); *A61B 5/0064* (2013.01);
(Continued)

(58) Field of Classification Search
CPC ................ A61B 5/11; A61B 5/0064; A61B 5/4806–5/4818
See application file for complete search history.

(56) References Cited

U.S. PATENT DOCUMENTS 5,914,660 A    6/1999    Mesibov et al.
6,062,216 A    5/2000    Corn
(Continued)

FOREIGN PATENT DOCUMENTS

CN    101044981 A    10/2007
CN    101966079 A    2/2011
(Continued)

OTHER PUBLICATIONS

Cuppens et al_2010_Automatic video detection of body movement during sleep based on optical flow in pediatric patients with epilepsy.*

(Continued)

*Primary Examiner* — Serkan Akar (57) ABSTRACT

Provided are systems (100) and methods (200) for providing contact-less sleep disorder diagnosis, including a sound input device (103) and/or a movement detector (105) that receive sound and/or movement data originating from a patient in a sleeping environment, respectively. Also included is a computer-implemented device (109) that receives and stores the sound and/or movement data and determines a sleep disorder diagnosis based on the received data.

36 Claims, 5 Drawing Sheets

(51) Int. Cl.
*A61B 7/00* (2006.01)
*A61B 8/00* (2006.01)
*A61B 5/113* (2006.01)

(52) U.S. Cl.
CPC .............. *A61B 5/11* (2013.01); *A61B 5/1128* (2013.01); *A61B 5/4812* (2013.01); *A61B 5/4815* (2013.01); *A61B 7/00* (2013.01); *A61B 7/003* (2013.01); *A61B 8/00* (2013.01); *A61B 5/1116* (2013.01); *A61B 5/1123* (2013.01); *A61B 5/1135* (2013.01); *A61B 5/4818* (2013.01)

(56) References Cited

U.S. PATENT DOCUMENTS

| | | | | |
|---|---|---|---|---|
| 6,352,517 | B1* | 3/2002 | Flock | A61B 3/113 600/558 |
| 8,542,878 | B2 | 9/2013 | Cennini | |
| 8,553,940 | B2 | 10/2013 | Kirenko et al. | |
| 8,666,116 | B2 | 3/2014 | Kirenko et al. | |
| 2006/0241359 | A1* | 10/2006 | Nagai | A61B 5/02416 600/301 |
| 2006/0279428 | A1* | 12/2006 | Sato | A61B 5/0064 340/575 |
| 2008/0156989 | A1* | 7/2008 | Du | G06F 3/017 250/338.1 |
| 2009/0062696 | A1 | 3/2009 | Nathan et al. | |
| 2009/0227888 | A1 | 9/2009 | Salmi et al. | |
| 2010/0102971 | A1 | 4/2010 | Virtanen et al. | |
| 2010/0152543 | A1 | 6/2010 | Heneghan et al. | |
| 2011/0021928 | A1 | 1/2011 | Glovangrandi et al. | |
| 2011/0311143 | A1 | 12/2011 | Cennini et al. | |
| 2012/0141000 | A1 | 6/2012 | Jeanne et al. | |
| 2013/0035599 | A1 | 2/2013 | De Bruijn | |

FOREIGN PATENT DOCUMENTS

| | | | |
|---|---|---|---|
| EP | 2278507 | A2 | 1/2011 |
| JP | 2005304941 | A | 11/2005 |
| JP | 2007289660 | A | 11/2007 |
| WO | 2006115832 | A2 | 11/2006 |
| WO | 2007143535 | A2 | 12/2007 |

OTHER PUBLICATIONS

Malakuti, K. "Towards an Intelligent Bed Sensor: Non-intrusive Monitoring of Sleep Disturbances via Computer Vision Techniques". Thesis submitted to Department of Electrical Engineering, University of Victoria, 2008, Canada.

Griffiths, C.J. et al. "A video system for investigating breathing disorders during sleep." New Techniques. Thorax 1991; 46: 136-140.

Frigola, M. "Vision Based Respiratory Monitoring System." Proceedings of the 10th Mediterranean Conference on Control and Automation—MED2002. Lisbon, Portugal, Jul. 9-12, 2002.

Sato, I. et al. "Non-contact Breath Motion Monitoring System in Full Automation". Proceedings of the 2005 IEEE, Engineering in Medicine and Biology 27th Annual Conference. Shanghai, China, Sep. 1-4, 2005.

Chazal, P. "Assessment of Sleep/Wake Patterns Using a Non-Contact Biomotion Sensor". 30th Annual International IEEE EMBS Conference Vancouver, BC, Canada, Aug. 20-24, 2008, p. 514-517.

De Haan, G. "True motion estimation with 3-D recursive search block matching". IEEE Transactions on Circuits and System for Video Technology, vol. 3, No. 5 Oct. 1993, pp. 368-379.

De Haan, G. "An efficient true motion estimator using candidate vectors from a parametric motion model". IEEE on Circuits and Systems for Video Technology, vol. 8, No. 1, Feb. 1998, p. 85-91. Transactions.

Greiner, J.C. "Object based motion estimation: a cost effective implementation". NatLab. Technical Note 2003/00573. Philips electronics Nederland BV. Issued Aug. 2003.

Flemons, W.W. Sleep related breathing disorders in adults: Recommendations for syndome definition and measurement techniques in clinical research. The Report of an American Academy of Sleep Medicine Task Force. Sleep. 1999; 22:667-89.

Molina, G. et al. "Practical Installation of a Video Actigraphy System", ID 670863. This was not filed.

De Bruijn, F. et al. "Remove respiration analysis", ID 671792. This was not filed.

Qiao, P. et al. "Orientation detection and body segmentation based on motion vector analysis for sleep", PR-TN 2009/00470.

* cited by examiner

CONTACTLESS SLEEP DISORDER SCREENING SYSTEM

This application is a national stage application under 35 U.S.C. § 371 of International Application No. PCT/IB2012/051474 filed on Mar. 28, 2012 and published in the English language on Oct. 4, 2012 as International Publication No. WO/2012/131589, which claims priority to U.S. Application No. 61/469,329 filed on Mar. 30, 2011, the entire disclosures of which are incorporated herein by reference.

The present disclosure pertains to systems and methods for sleep disorder diagnosis and/or screening, and, in particular, systems and methods for sleep disorder diagnoses and/or screening that do not contact a patient.

Typical screening/diagnosis for sleep disorders includes obtrusive measurements obtained though various devices/sensors attached to a patient as well as visits to a "sleep clinic" (e.g., for mounting and dismounting of the sensors, in-patient monitoring, etc.). These procedures are both time and effort consuming for the sleep clinicians (e.g., requiring overnight shifts) and patients alike (e.g., uncomfortable and unfamiliar sensors and sleep settings). Furthermore, waiting lists for sleep screening are common.

Accordingly, a contactless home screening system for sleep disorders that can be installed easily by the patient with no mounting of on-body sensors would be advantageous.

Accordingly, it is an object of one or more embodiments of the present invention to provide a system for providing sleep disorder diagnosis comprising: a sound input device that receives sound originating from a patient in a sleeping environment; a movement detector that monitors movement of the patient in the sleeping environment; and a computer-implemented device configured to: receive and store data relating to the sound originating from the patient, receive and store data relating to the movement of the patient, and determine a sleep disorder diagnosis based on one or more of the data relating to the sound originating from the patient or the data relating to the movement of the patient.

It is yet another aspect of one or more embodiments of the present invention to provide a method for providing sleep disorder diagnosis comprising: receiving, at a sound input device sound originating from a patient in a sleeping environment; monitoring, at a movement detector, movement of the patient in the sleeping environment; and determining, at a computer implemented device, a sleep disorder diagnosis based on one or more of the sound originating from the patient or the movement of the patient in the sleeping environment.

It is yet another aspect of one or more embodiments to provide a system for providing sleep disorder diagnosis comprising: sound input means for receiving sound originating from a patient in a sleeping environment; movement detecting means for monitoring movement of the patient in the sleeping environment; computer-implemented means for: receiving and storing data relating to the sound originating from the patient, receiving and storing data relating to the movement of the patient; and determining a sleep disorder diagnosis based on one or more of the data relating to the sound originating from the patient or the data relating to the movement of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The systems and methods described herein enable circumvention of typical sleep disorder diagnostic processes. They provide sleep disorder screening procedures having advantages over conventional procedures in terms of cost, convenience, time, and other advantages. For example, as discussed herein, typical screening for sleep disorders requires obtrusive sensors attached to the patient and often visits to a "sleep clinic" (e.g., for mounting and dismounting of the sensors, in-patient monitoring, etc.). Ambulatory screening is not very convenient for the patient because the patient needs to be wired up with polysomnography (PSG) sensors and/or other sensors (typically by a clinician). These procedures are both time and effort consuming for the sleep clinicians (e.g., requiring overnight shifts) and patients alike (e.g., uncomfortable and unfamiliar sensors and sleep settings).

The systems and methods provided herein address the need of easier overall screening to diagnose sleep disorders. Existing solutions are time and effort consuming and do not screen for multiple disorders at the same time. The systems and methods described herein offer differential diagnosis during home (or other convenient sleeping area) screening, which allows the user to sleep in the natural sleeping environment without any on-body sensors disturbing sleep.

Multiple groups can derive benefit from the systems and methods described herein such as, for example, general practitioners (GP—physicians). Diagnosis of a sleep problem may be difficult because of the reliance on subjective data of the client and/or requirement of conducting a sleep study to diagnose. GPs are usually not sleep experts, and in cases of severe problems, they refer the patient to a sleep lab to be diagnosed. The systems and methods described herein may reduce the need for diagnosis in a sleep lab, and improve the quality of the referral of the GP to a sleep lab, hence reducing the number of patients on the waiting lists.

Sleep clinics themselves may benefit from the systems and methods described herein. Preparation for conventional home screening in a lab setting is time and cost consuming, as many on-body sensors (which may require lab specialists to apply) are used. The unobtrusive home tests enabled by the systems and methods provided herein may be used as initial screening and provide low preparation effort and low cost through the use of off-body sensors. Additionally, the time and effort to come to a differential diagnosis can be reduced by utilizing automatic computer-implemented analysis. Furthermore, waiting lists may be shortened, as patients that do no classify for intramural (in clinic) research will not occupy the facilities and staff.

Patients will also benefit from the systems and methods described herein. Testing in a real, home environment without the use of 'wires' attached to the patient is more convenient for the patient, as the patient will no longer need to travel from and to the sleep clinic and sleep with wires attached or attempt to sleep at the sleep clinic itself. Moreover, it is well known that sleep in a sleep clinic itself deviates from the sleep one experiences in their own sleeping environment. From user insights it is known that people suffering from sleep difficulties want insight into their sleep. Patients seek confirmation that their sleep is as bad as they think, and they want to understand the reason for their (subjectively) bad sleep. Furthermore, patients want to be assured that they are the reason that their partner is disturbed during sleep. Patients also want to know what is going on during sleep so as to evaluate whether to seek the help of a physician (GP or sleep specialist).

Figure 1:
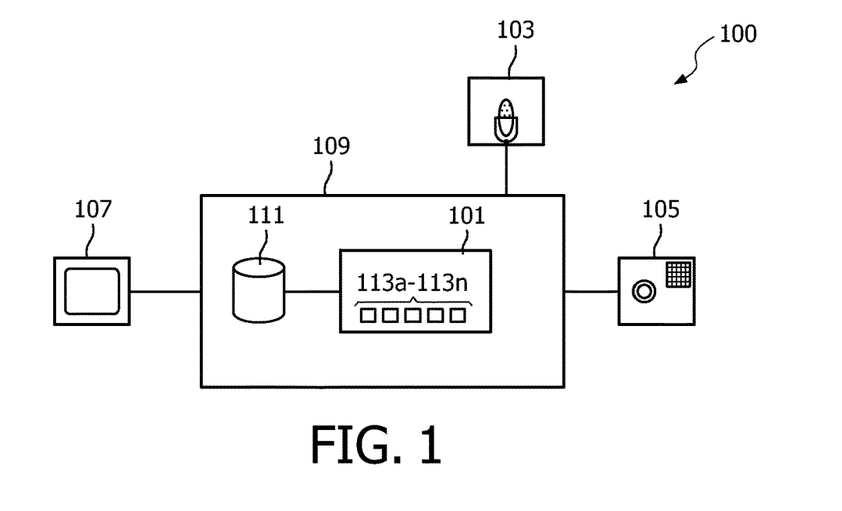
FIG. 1 is an example of a system for sleep disorder diagnosis, according to various embodiments of the invention.

In some embodiments, systems for contactless sleep disorder diagnosis/screening are provided. FIG. 1 illustrates a system 100, which is an example of a system for contactless sleep disorder diagnosis/screening. System 100 may include control application 101, a sound input device 103, a movement detector 105, a display device 107 and/or other elements.

Control application 101 may be or include a computer application that enables data receipt, data processing, data output, and or other features and functions described herein. Control application may be executed on or otherwise supported by one or more computer-implemented devices such as, for example, computer-implemented device 109. Computer implemented device 109 may include one or more processing devices (e.g., microprocessors), one or more associated memory devices (e.g., memory 111), a plurality of input and/or output ports, and/or other elements enabling computing capability.

Sound input device 103 may be or comprise a microphone or other device that enables receipt of sound from an environment wherein a patient is sleeping and conversion of this sound into electrical and/or electromagnetic signals. In some embodiments, sound input device 103 may include or comprise a plurality of microphones or other sound receiving devices positioned so as to optimally or precisely obtain sound from a patient and/or their sleep environment as described herein.

Movement detector 105 may be or comprise a light detecting camera or other optical sensor, a radar device, infra-red detection device, heat detection device, ultrasound device, and/or any other sensor capable of detecting movement of a patient in a sleeping environment without contact with the patient. The movement detected may include eye movement, chest movement, mouth movement, leg and/or arm movement, torso movement, and/or other bodily movement. In some embodiments, movement sensor may include or comprise a plurality of movement detectors (e.g., cameras, radar devices, etc.) so as to optimally or precisely obtain movement information from a patient as described herein. In some embodiments, movement detector 105 may include or may be used with a light source that enables better visualization of the movements of a patient.

Figure 5:
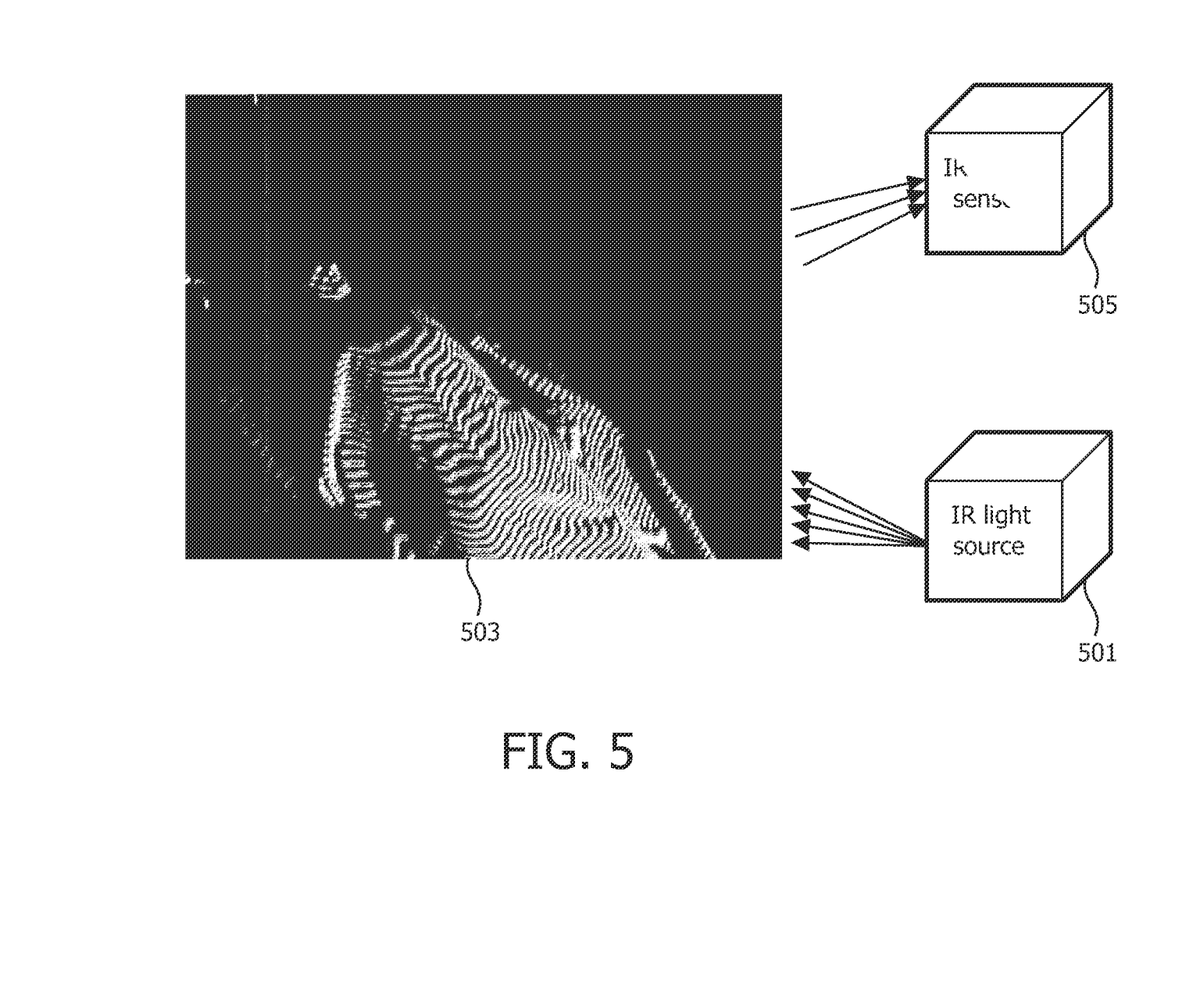
FIG. 5 is an example of a movement detector utilizing structured light, according to various embodiments of the invention.
Figure 6A:
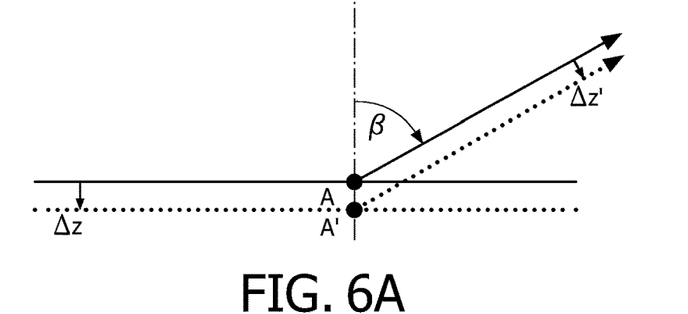
FIGS. 6A and 6B illustrate examples of the geometry of light rays used to detect movement, according to various embodiments of the invention.
Figure 6B:
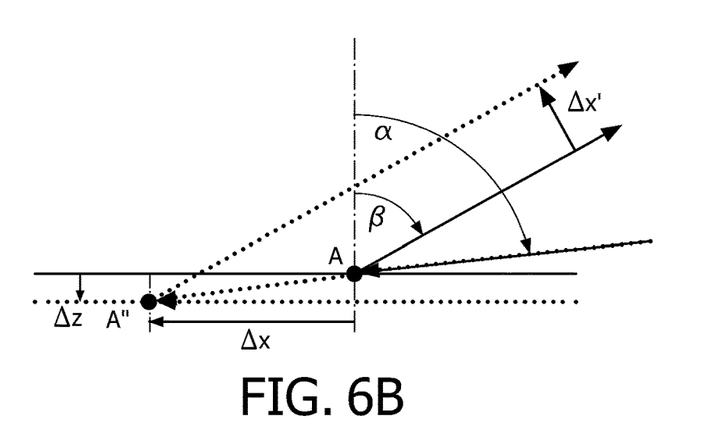

In some embodiments, the light source may project structured light onto a patient. The use of structured light may include projecting an infrared light pattern on the patient which deforms when the subject moves/breathes. The deformation due to micro movement (e.g., breathing) can then be easily measured. FIG. 5 illustrates an example of a movement detector 500, including a structured light source 501 which projects a pattern of infrared light onto a patient 503, which is then detected by sensor 505. The method used to detect movement may be comparable to phase shifting interferometry, which is used for quantification of depth. High motion detection is achieved by creating a baseline distance between the structured light source and a sensor that senses light from the structured light source reflected off of the patient. FIGS. 6A and 6B illustrate an example of the geometry of light rays (approximated by parallel bundles assuming the structured light source and its corresponding sensor are sufficiently spaced from one another) used in detecting movement of a patient. FIG. 6A illustrates movement of a point on the surface of a patient from A to A'. When observed by a sensor under an angle $\beta$, an apparent shift is recorded over distance $\Delta z'$. FIG. 6B illustrates an instance wherein incident light is projected at an angle $\alpha$ and observed from an angle $\beta$. Under a vertical shift $\Delta z$ of the surface, projected point A shifts over a distance $\Delta x$ to point A'', which is observed as an apparent shift of $\Delta x'$ projected in the direction of the sensor. It is clear that distance $\Delta x'$ is much larger than $\Delta z'$, such that smaller vertical motions can be detected. In absence of a projected pattern, as shown in FIGS. 6A and 6B, the relation between observed vertical shift $\Delta z'$ and the real vertical shift $\Delta z$ (from A to A') is given by: $\Delta z' = \Delta z \sin \beta$. In case point A, the result of a projection from an angle $\alpha$, the relation between observed horizontal shift $\Delta x'$ and the real vertical shift $\Delta z$ (from A to A'') is given by: $\Delta x' = \Delta z \tan \alpha \cos \beta$. The advantage of the angulated projection can be expressed in terms of an increase of distance of the shifting phenomena as they appear on the sensor. In this case, the gain G would be the ratio of the new displacement over the old displacement:

$$G = \frac{\Delta x'}{\Delta z'} = \frac{\Delta z \tan \alpha \cos \beta}{\Delta z \sin \beta} = \frac{\tan \alpha}{\tan \beta}.$$

Clearly, the gain G from projected light patterns is maximized when projection angle α is as large as possible, almost parallel to the surface, and observation angle β is as small as possible, preferably with the sensors optical axis perpendicular to the surface. However, already small distances between the camera and the light source are sufficient to monitor breathing movements.

In some embodiments, a light source and sensor that form movement detector 105 may be within a single housing. In some embodiments, movement detector 105 maybe such that no light source is needed (e.g., radar, heat detector, ultrasound device, etc.). In some embodiments, movement detector may include additional detectors which may be used to derive movement data. For example, in some embodiments, movement detector 105 may include a first movement detector used to detect body movement, and a second movement detector used to detect facial movement. Other configurations may also be used.

In some embodiments, display device 107 may be or include a display screen such as, for example, a liquid crystal display (LCD) screen, light emitting diode (LED) display screen, cathode-ray based display screen, or other type of display device. In some embodiments, display device 107 may be or include other devices capable of outputting information regarding data received and/or determined by control application 101. For example, in some embodiments, display device may be a printer or speaker that provides information via printouts or sound output. In some embodiments, wherein playback of data regarding a patient's sleep is enabled, a speaker may be combined with a visual display device (e.g., a display screen) as display device 107.

In some embodiments, sound input device 103, movement sensor 105, and display device 107 may be operatively connected to computer-implemented device 109 and/or control application 101. These connections may be wired, wireless and or a combination thereof. In some embodiments, sound input device 103, movement sensor 105, and/or display device 107 need not be integrated with computer implemented device 109 or control application 101, but may be modular devices that gather sound and/or movement data, respectively (including storing such on their own local memory). The data may then be communicated to control application 101 after having been placed in connection therewith at a later time. In some embodiments, computer-implemented device 109 (including control application 101 and/or memory 111), sound input device 103, movement sensor 105, display device 107, and/or other elements may be integrated together as a single device. In some embodiments, one or more of computer-implemented device (including control application 101), sound input device 103, movement detector 105, display device 107, and/or other elements may be integrated into a single housing. In some embodiments, computer-implemented device 109 (including control application 101 and/or memory 111) and movement detector 105 may be integrated into a single housing, while sound input device 103 may include a separate element that can be placed proximal to a sleeping patient but which can provide data to control application 101 and/or memory 111 via a wire line connection, a wireless connection, or a subsequent coupling with computer-implemented device 109.

Control application 101 may include one or more modules 113a-113n. One or more software modules 113a-113n may be one or more software modules comprising computer-executable instructions, routines, algorithms, or other data that enable the various features and functions described herein. For example, one or more modules 113a-113n may receive and store (e.g., in memory 111) data relating to sound from a patient (and/or the sleeping environment of the patient) from sound input device 103; receive and store (e.g., in memory 111) data relating to movement of a patient from movement detector 105; perform one or more calculations, comparisons, or determinations using received sound and/or movement data; outputting one or more sleep disorder diagnoses or other data (e.g., on display device 107); and/or performing other features or functions. The instructions of modules 113a-113n may be stored on a hard disk, EPROM, EEPROM, other non-volatile memory, or other memory/storage device (e.g., memory 111) that is operatively connected to or in communication with the one or more processors of computer-implemented device 109 and/or other processors supporting/running control application 101.

Figure 2:
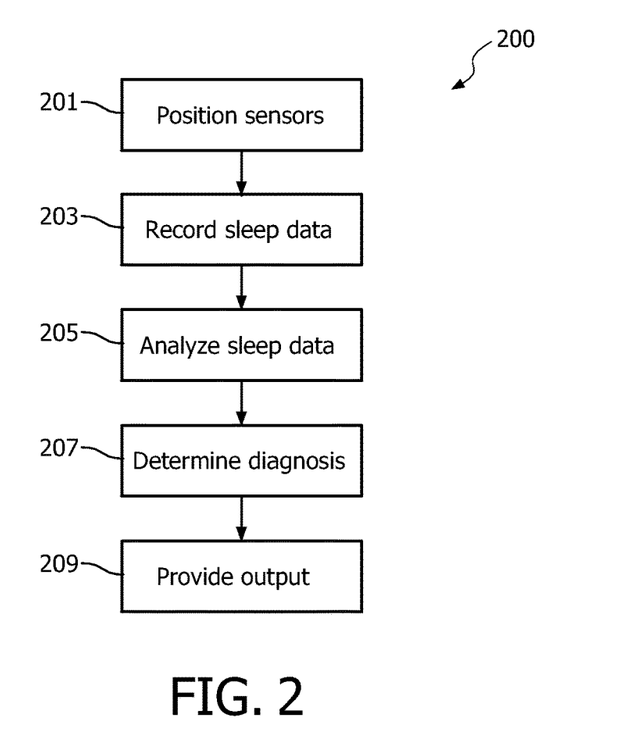
FIG. 2 is an example of a method for sleep disorder diagnosis, according to various embodiments of the invention.

In some embodiments, processes for contactless sleep disorder diagnosis/screening are provided. FIG. 2. illustrates a process 200, which is an example of a process for contactless sleep disorder diagnosis/screening. Process 200 includes an operation 201, wherein one or more sensors are positioned in a sleeping environment of a patient. For example, in one embodiment, sound input device 103 and movement detector 105 of system 100 may be positioned in the home bedroom of the patient. In some embodiments, sound input device 103 may be positioned (e.g., by the patient) so that sound from the patient and sound from the sleeping environment (e.g., outdoor noise, ventilation, etc.) can be detected, and movement detector 105 may be positioned so that movement of the patient in the sleeping environment can be detected. For example, in some embodiments, sound input device 103 may be positioned close to a bed where the patient is sleeping so as to record the sound made by the patient. In some embodiments, sound input device 103 may be placed, for example, on a bedside table of the patient or otherwise placed so as to detect sound in the patient's sleeping environment. In some embodiments, movement detector 105 may be positioned so that the patient is fully within its field of view/line of sight (e.g., on a bedside table, mounted on a ceiling or wall of the patient's bedroom, in or on a cupboard/dresser, on its own stand, or other placements). As described herein, in some embodiments, movement sensor may include or may be used with a light source that projects structured light on the patient. This light source may be placed in close proximity to movement detector 105 or otherwise positioned to project light onto a patient so that movement detector 105 optimally detects movement of the patient as described herein.

In an operation 203, the one or more sensors may receive sound and movement data of the patient in the sleeping environment. In some embodiments, this may include multiple nights of data. As such, the sensors may be turned on and off (or data recording turned on or off) multiple times during the data recording process. For example, in some embodiments, sound input device 103, movement sensor 105, and/or computer-implemented device 107 may include one or more buttons, toggle switches, or other input devices enabling the patient or other user to turn data recording on or off. In some embodiments, one or more of modules 113a-113n may receive and store (e.g., in memory 111) sound data regarding the patient in the sleeping environment from sound input device 103 and movement data regarding the patient in the sleeping environment from movement detector 105.

In an operation 205, the received sound and/or movement data may be analyzed to extract data regarding the occurrence of one or more events during the patient's sleep and/or one or more parameters of the patient's sleep. Sleep events may include, for example, snoring events (including duration and severity), speech, tooth grinding, cessation of breathing (including length of each episode), sleep/wakefulness cycles, eye movement, body movement (e.g., arm, torso, leg), respiratory rate, respiratory flow, heart rate, and/or other events or characteristics. For example, one or more of modules 113a-113n may utilize the received sound data to determine snoring events, speech, tooth grinding, etc. In another example, one or more of modules 113a-113n may utilize the received movement data to determine limb movement events. In some embodiments, one or more of modules 113a-113n may utilize sound and movement data to determine parameters/events such as respiration (and parameters thereof), sleep/wakefulness cycles, and/or other events/parameters.

Figure 3:
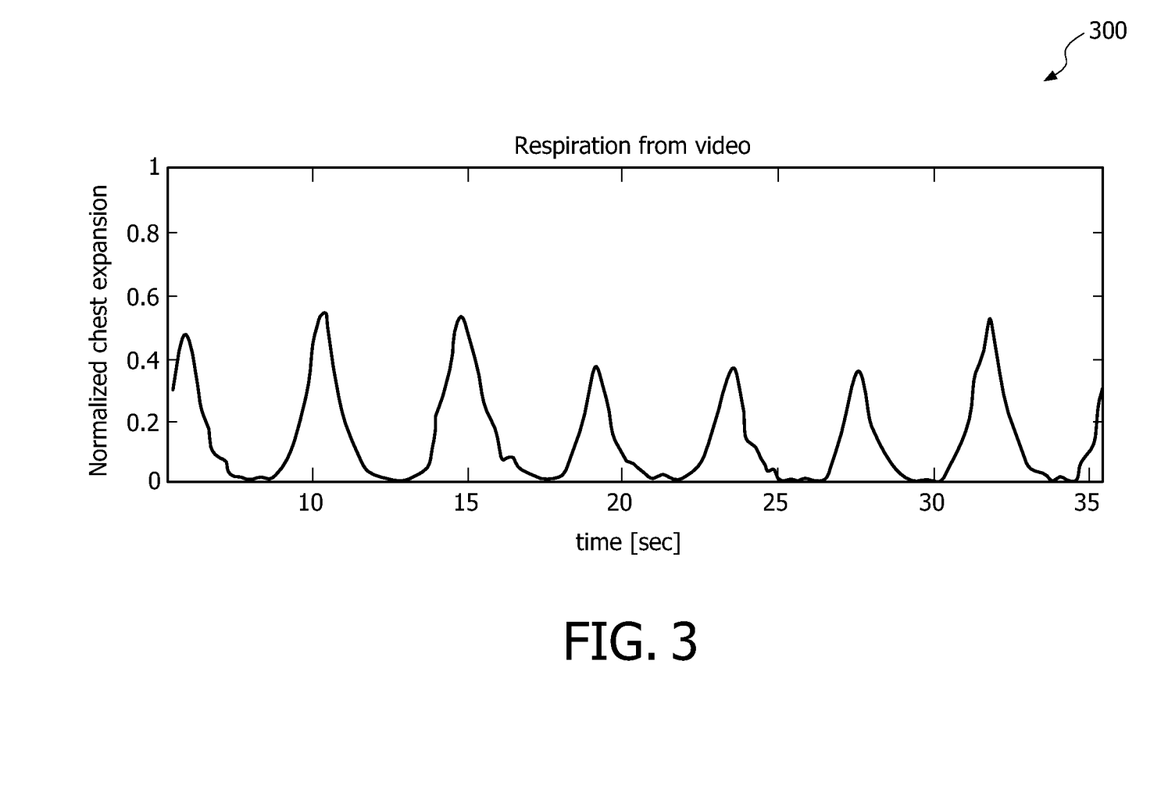
FIG. 3 is an example of a breathing wave form, according to various embodiments of the invention.

As described herein, one or more of modules 113a-113n may utilize received sound and movement data to determine breathing parameters such as, for example, breathing rate, inhale/exhale transitions and expiratory pauses, and/or other parameters. These parameters may be used to produce an approximation of a breathing wave form resembling the air flow of a patient's respiration. FIG. 3 illustrates a graph 300, which is a plot of chest expansion (i.e., movement data) over time that approximates a typical breathing wave form produced for a person lying on his/her belly. This wave form and data extracted from it can be used in providing diagnosis of one or more sleep disorders, e.g., as described herein.

One or more of modules 113a-113n may perform body motion estimation for the patient (and, in some instance, his/her partner) using information from movement sensor 105. Various motion estimation algorithms with a rather low computational complexity can be used. In some embodiments, images derived from data detected by movement detector 105 may be constructed that provide coded (e.g., color coded or otherwise coded) indication of motion vectors. These vectors give an accurate indication of direction and amplitude of patient motion. The motion vectors can be used to extract the following information: 1) orientation of the sleeping person; 2) rough segmentation of body parts of sleeping person; 3) segmenting patient from bed partner; 4) analysis of the local motion (relevant for, e.g., PLM detection) by analyzing the motion vectors in the segmented areas. From the movement information, time data associated with the movement information and/or other information, sleep parameters such as wake vs. sleep, sleep efficiency, sleep onset latency and wake after sleep onset, and/or other parameters/events can be derived.

In an operation 207, the one or more determined events/characteristics are utilized to determine at least one diagnosis (which may be a preliminary diagnosis) for the patient. In some embodiments, the determination may be or include calculation of a probability (e.g., a percentage indicator) that a given sleep disorder is present in a patient. The determination of operation 207 may be based on correlations, models, routines, or other information known regarding sleep disorders. For example, in some embodiments, the calculation/determination of operation 207 may be performed by one or more of modules 113a-113n using one or more processors of computer-implemented device 109. In some embodiments, memory 111 or other data storage accessible to modules 113a-113n may store correlations, models, routines, or other information that can be used, along with the determined events/parameters of operation 205 to provide a sleep disorder diagnosis and/or probability. As discussed herein, information regarding different events/parameters of a patient's sleep may be used with different models, routines, etc. to provide a diagnosis.

For example, typical methods used to detect obstructive sleep apnea (OSA) during sleep utilize polysomnography (PSG—also referred to as a "sleep study"). The measurements involved in PSG for OSA typically include: recording of brain activity via glued sensors on the skull; recording of eye movement and other muscle activity via glued sensors on the skin; recording of breathing and heart rate (via contact sensors); recording of respiratory flow via a sensor mounted next to nostrils; recording of blood saturation level (SpO2); and observing sleep position (typically observed by clinician and/or sleep technician). Conventional diagnosis of OSA during sleep further includes detection of cessation of airflow (e.g., a complete obstruction for at least 10 seconds) with a concomitant 2 to 4 percent drop in arterial oxygen saturation. Conventional diagnosis of OSA also may include detection of hypopnea, which is a reduction in airflow of at least 30 to 50 percent with a drop in oxygen saturation. OSA parameters reported during standard polysomnography include the apnea-hypopnea index (AHI), which is the average number of apneas (cessations of breathing) and hypopneas per hour of sleep. OSA severity is then classified on the basis of the patient's AHI score, into three categories: mild (AHI score between 5 and 15), moderate (AHI score between 15 and 30) and severe (AHI score greater than 30).

The systems and methods described herein avoid conventional PSG devices and procedures for OAS or snoring detection through the use of the contactless sensors described herein to detect various parameters/events such as, for example, respiratory airflow (which can be estimated using determined respiration parameters; see e.g., FIG. 3) and respiratory effort through automatic (computer-implemented) analysis of data from these sensors during sleep. In some embodiments, respiratory effort can be determined from a breathing waveform (see e.g., FIG. 3) and a motion analysis of the patient's chest region. For example, as described above with respect to operation 205, received data from sound input device 103 and movement monitor 105 may be analyzed by one or more of modules 113a-113n to determine sufficient information on breathing parameters of the patient (see e.g., FIG. 3) to come to an initial differential diagnosis with regards to sleep-disordered breathing (e.g., OSA). Again referring to the process 200, the determined parameters/events relating to the patient's sleep may be used by one or more of modules 113a-113n in operation 207, to provide a sleep disorder diagnosis for the patient. For example, respiration parameters may be used to determine a patient's Apneu Hypopnea Index, which may be used to classify a severity of a patient's OSA. Sound data can also be used for an OSA diagnosis. For example, the changes in amplitude of a patient's breathing noise during sleep may be used to determining when a breathing cessation occurs.

With respect to the disorder of periodic limb movements (PLM) during sleep, conventional diagnostic techniques include polysomnography (PSG) combined with additional sensors specifically designed for PLM. For example, in some instances, movement sensors and/or electromyography (EMG) sensors may be attached to the patient's limbs. Electromyography is a technique for evaluating and recording the electrical activity produced by skeletal muscles. It records electrical potential generated by muscle cells when these cells are electrically or neurologically activated. EMG measurement can be performed by most typical PSG devices. Typical recording of PLM involves EMG surface electrodes placed in one or more anterior tibialis muscles and/or recording of movement of the legs via accelerometry. In another instance, conventional PSG for PLM may include recording of brain activity via glued sensors on the skull, recording of eye movement and other muscle activity via glued sensors on the skin, recording of muscle activity in the legs via glued sensors on the legs, recording of movement of the legs via sensors attached to the legs, and/or the use of other sensors/metrics. Conventional diagnosis of PLM during sleep (PLMS) includes determining the existence of bursts of muscle activity during sleep with a duration of 0.5-5 seconds, occurring in a series of four movements or more with an interval of 5-90 seconds in between. In some embodiments, each movement has to be at least 25% of the amplitude of an EMG calibration signal. PLM parameters reported during standard polysomnography are also used such as, for example, the number of PLMS (total number of periodic limb movements during sleep), the number of arousal-associated periodic limb movements (PLMA), the number of periodic limb movements associated with respiratory events. A PLM index (number of periodic limb movements per hour of sleep) and a PLM arousal index (number of arousal-associated periodic limb movements per hour of sleep) may be produced for a patient and used for diagnosis of PLM.

Figure 7:
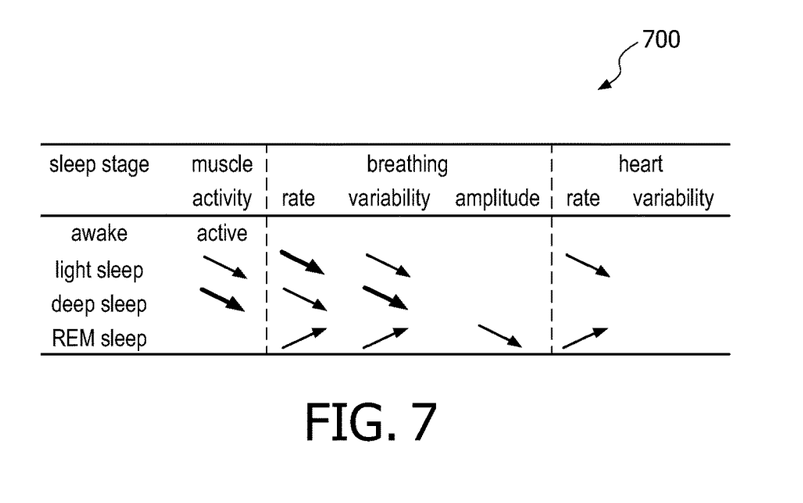
FIG. 7 is an example of a chart illustrating the correlation between certain physiologically measurable phenomena and sleep state, according to various embodiments of the invention.

The systems and methods described herein avoid these conventional elements and procedures. For example, as the PLM index may be a significant parameter for diagnosis, one or more of modules 113a-113n may, in operation 207, perform automatic PLM index determination for a patient, based on the movement and sound data analyzed in operation 205. For example, recorded movements and sound accompanying those movements may be used, in operation 205, to determine the frequency and severity of limb movements and/or whether such movements result in arousal. This data may be used to produce PLM or PLMA index for the patient and therefore a diagnosis (e.g., in operation 207). Other information relating to the sound and movement of a patient during sleep may be used for such a diagnosis. For example, PLMs are most common during light sleep, less frequent during deeper sleep, and rare during REM (rapid eye movement) sleep. With this knowledge, the one or more of modules 113a-113n can utilize sound and movement data (including the temporal natures of both—e.g., when they occurred in the night or in relation to arousal events) to determine whether it is likely that a given movement is an instance of PLM using information or a determination of whether the patient is in a light sleep (e.g., more pronounced movement events), deep sleep (e.g., reduced movement events), REM sleep (e.g., eye movement), or other sleep phase based on limb movement, breathing characteristics, and/or other data. Sleep phase can be determined using phenomena measurable using the systems described herein. FIG. 7 illustrates a chart 700 which illustrates different physiologically measurable phenomena and their relationship to a sleep state determination. Light sleep can be characterized by relatively more episodes of movement (in general around 40% of the sleep time; mostly in between episodes of deep sleep and REM sleep—and vice versa). Deep sleep can be characterized by relatively large episodes of no movement (in general, more prominent in the first half of sleep time, mostly preceded and followed by an episode of lighter sleep). REM sleep can be characterized by episodes of eye movement and no body movement (in general more prominent in the second half of sleep time, mostly preceded and followed by an episode of light sleep).

With respect to insomnia disorder, conventional diagnostic techniques are often based on subjective complaints of "not being able to sleep" and "feeling tired during the day." However, accurate insomnia diagnosis requires much more information such as, for example, sleep history, duration of the problems, and/or behavioral and cognitive factors. Diagnosis may not be based solely on objective parameters, but these can provide insight into the actual sleep architecture of an insomniac and the incidence of sleep-state mispercептions (i.e., sleep state misperception is a diagnostic term adopted in the International Classification of Sleep Disorders (American Sleep Disorders Association 1990) to replace two previously used diagnostic categories of sleep disorders: subjective insomnia complaint without objective findings and subjective sleepiness complaint without objective findings.). However, objective detection of insomnia often includes polysomnography (PSG), which, as described herein, includes recording of eye movement and other muscle activity via glued sensors on the skin and recording of breathing and heart rate via attached sensors. Common sleep parameters used in polysomnography for insomnia include: total sleep time (TST); sleep-onset latency (SOL); number of nocturnal awakenings (NOW); time awake at night or wake after sleep onset (WASO); and sleep efficiency (SE; which is total sleep time/time in bed).

The systems and methods described herein avoid conventional PSG devices and procedures for objective insomnia analysis. For example, as sleep efficiency, sleep onset latency, and wake after sleep onset may be significant parameters, one or more of modules 113a-113n may in operation 207, perform automatic sleep quantification of these parameters based on based on the movement and sound data analyzed in operation 205. These parameters can be determined using a temporal parameter of sound and/or movement data and the occurrence of certain events (e.g., sleep onset, awakenings, etc.). The incidence of rather poor scores on the sleep quantification parameters, whilst excluding apnea and restless legs can be considered indicative for insomnia and therefore used during objective insomnia analysis.

Parasomnias are a category of sleep disorders that involve abnormal and unnatural movements, behaviors, emotions, perceptions, and dreams that occur: while falling asleep, sleeping, between sleep stages, or arousal from sleep. A range of parasomnias exist that are related to movement and/or breathing during sleep. Sleepwalking (somnambulism) is an example of a parasomnia, and has a prevalence of 1-17% in childhood, with the most frequent occurrences around the age of eleven-twelve. About 4% of adults experience somnambulism.

Another example of a parasomnia include sleep terrors (night terrors), which are the most disruptive arousal disorder, since they may involve loud screams and panic; in extreme cases, they may result in bodily harm or property damage (e.g., by running about or hitting walls).

Bruxism (teeth grinding) is another example of a parasomnia. Bruxism is a common sleep disorder where the sufferer grinds their teeth during sleep. This can cause sleep disruption for the sufferer and bed partner, wear and fracture of teeth, jaw pain, and other problems.

Another parasomnia is rapid eye movement (REM) sleep behavior disorder. REM Sleep Behavior Disorder is the most common REM sleep parasomnia in which muscle atonia (i.e., sleep induced muscle paralyzation) is absent. REM sleep disorder allows the individual to physically act out their dreams, which may result in repeated injury (e.g., bruises, lacerations and fractures) to themselves or others. Patients may take self-protection measures by tethering themselves to bed, using pillow barricades or sleeping in an empty room on a mattress. Catathrenia is a rapid eye movement sleep parasomnia consisting of breath holding and expiratory groaning during sleep. It is distinct from both sleep talking and obstructive sleep apnea. The sound is produced during exhalation as opposed to snoring which occurs during inhalation. It is usually not noticed by the person producing the sound but can be extremely disturbing to sleep partners (sufferers tend to be woken up by their own groaning as well). Bed partners generally report hearing the person take a deep breath, hold it, then slowly exhale; often with a high-pitched squeak or groaning sound.

In some embodiments, the systems and methods described herein may be used to diagnose these or other parasomnias. For example, one or more of modules 113a-113n may, in operation 207, analyze large and small movements determined in operation 205 (e.g., movement data) as well as audio information collected during sleep. This information may be used to identify parameters that are indicative of the above parasomnias such as, for example, loud screens, sleep walking, acting out dreams, teeth grinding, or other indicators.

Figure 4:
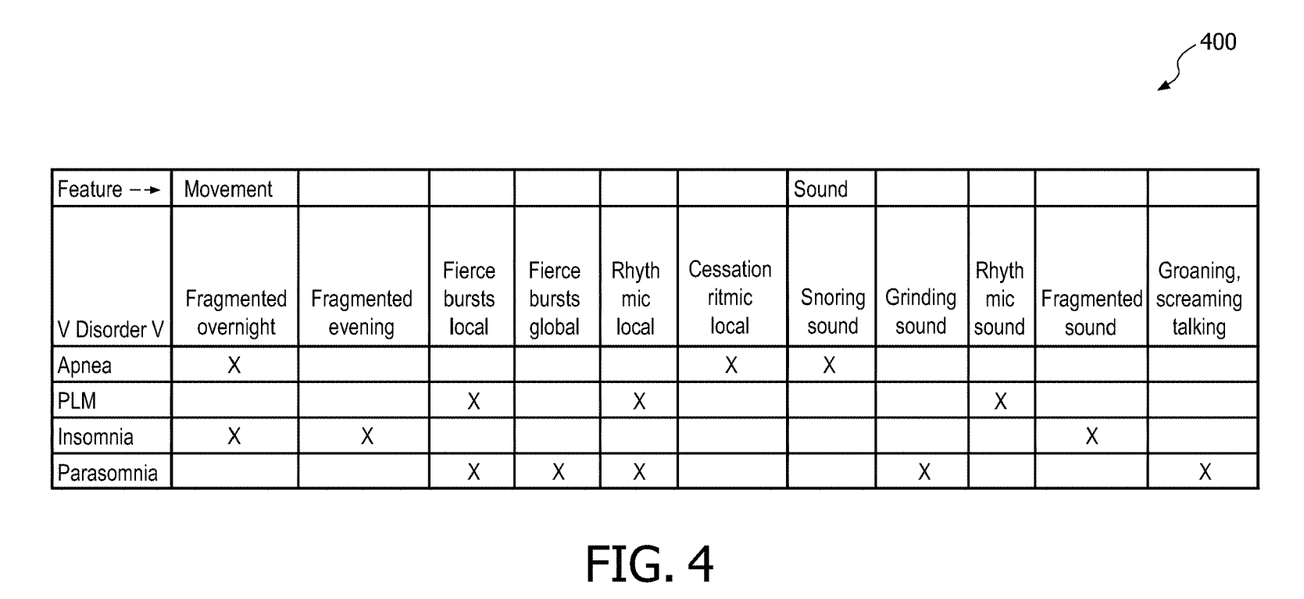
FIG. 4 is an example of a chart used for determining a diagnosis from sleep events/parameters, according to various embodiments of the invention.

As described herein, the determination of operation 207 may be based on the occurrence of different distinct events/parameters determined (in operation 205) from received sound and/or movement data are used in performing a diagnosis. FIG. 4 illustrates a table 400, which is an example of a chart that can be used (e.g., by one or more of modules 113a-113n) to provide a diagnosis based on event/parameter inputs. Note that in table 400, some of the features might load on several diagnostic profiles. However, in some embodiments, a given diagnosis need not be solely dependent on one feature and hence other features provide the discriminating power. In some instances, information regarding movement may dramatically increase the discriminating power for some diagnoses. For example, detection of cessation of rhythmic movement in chest area may increase the probability of an apnea diagnosis. Detection of rhythmic movements in the leg area may increase the probability of a PLM diagnosis, while they only slightly bear on a parasomnia diagnosis. Note that the list of features illustrated in chart 400 is not exhaustive. Other features can be detected and used In an operation 209 of process 200, the determination of operation 207 may be output to a patient and/or doctor. For example, in some implementations, one or more of modules 113a-113n may produce a display of the diagnosis that can be presented to a patient, doctor, or other person via display device 107. In some embodiments, the display or the diagnosis can be transmitted to a computer at doctor's office or other remote computer (e.g., a web-accessible server where the information can be downloaded for sharing with one or more doctors or other persons). In some embodiments, a probability associated with a diagnosed sleep disorder and/or any calculated indices for a patient (e.g., AHI, PLM index, PLMA index) may be provided/displayed. In some embodiments, one or more of modules 113a-113n may save/log (e.g., in memory 111) events which give rise to a potential diagnosis (e.g., of PLMS, apnea, insomnia, parasomnia, etc.) and/or the raw data they are derived from. These events/data can be played back for patient and/or clinicians if desired (e.g., using display device 107 or other display device).

In some embodiments, tangible computer-readable media comprising computer-executable instructions for causing one or more computer processors to perform one or more of the features and functions set forth herein, including the operations of the methods described herein, may be provided.

The systems described herein are exemplary system configurations. Other configurations may exist. Those having skill in the art will appreciate that the invention described herein may work with various configurations. Accordingly, more or less of the aforementioned system components may be used and/or combined in various embodiments. It should also be understood that various software modules 113a-113n that are utilized to accomplish the functionalities described herein may be maintained on different components than computer-implemented device 109, as desired or necessary. In other embodiments, as would be appreciated, the functionalities described herein may be implemented in various combinations of hardware and/or firmware, in addition to, or instead of, software. Furthermore, various operations of the methods described herein, while described in a particular order, may be performed in different orders as would be appreciated by those having skill in the art. In some embodiments, more of less of the described operations may be used.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to monitor a sleep session of a patient without making physical contact with the patient, the system comprising:
   a sound sensor configured to generate output signals that convey information related to sound originating from the patient in a sleeping environment;
   a movement sensor comprising:
      a light source configured to project a structured light pattern onto the patient which deforms when the patient moves; and
      a detector configured to receive light reflected from the patient, the detector configured to generate output signals that convey information related to changes in the structured light pattern projected onto the patient caused by movement of the patient; and
   one or more hardware processors configured by machine-readable instructions to:

receive and store data relating to the sound originating from the patient based on the information conveyed by the output signals from the sound sensor, determine movement of the patient based on (1) a distance between the light source and the detector, and (2) a change in angle of reflected light from the structured light pattern received from an individual moving point on the patient, wherein images derived from the information related to changes in the structured light pattern are construed wherein an indication of motion vectors is provided, wherein the motion vectors indicate a direction and an amplitude of the movement of the patient, wherein the motion vectors facilitate segmentation of one or more body parts, and wherein information related to a mouth movement is determined based on the segmentation of the one or more body parts, and determine a sleep disorder diagnosis based on the sound originating from the patient and the movement of the patient, wherein the one or more hardware processors are configured to determine parasomnia Bruxism based on the determined mouth movement.

2. The system claim 1, wherein the detector comprises one or more of a visible light detecting camera or an infrared light detecting camera.

3. The system of claim 1, wherein neither the sound sensor nor the movement sensor is in contact with the patient when sound is received or movement is monitored.

4. The system of claim 1, wherein at least one of the sound sensor or the movement sensor is integrated into a housing with the one or more hardware processors.

5. The system of claim 1, wherein the determination of the sleep disorder diagnosis includes a probability indicator for the diagnosis.

6. The system of claim 1, wherein the motion vectors facilitate one or more of a determination of an orientation of the patient, a segmentation of the patient from a bed partner, and an analysis of a local motion.

7. A system configured to monitor a sleep session of a patient without making physical contact with the patient, the system comprising:
   a sound sensor configured to generate output signals that convey information related to sound originating from the patient in a sleeping environment;
   a movement sensor comprising:
      a light source configured to project a structured light pattern onto the patient which deforms when the patient moves; and
      a detector configured to receive light reflected from the patient, the detector configured to generate output signals that convey information related to changes in the structured light pattern projected onto the patient caused by movement of the patient; and
   one or more hardware processors configured by machine-readable instructions to:
      receive and store data relating to the sound originating from the patient based on the information conveyed by the output signals from the sound sensor,
      determine movement of the patient based on (1) a distance between the light source and the detector, and (2) a change in angle of reflected light from the structured light pattern received from an individual moving point on the patient, wherein images derived from the information related to changes in the structured light pattern are construed wherein an indication of motion vectors is provided, wherein the motion vectors indicate a direction and an amplitude of the movement of the patient, wherein the motion vectors facilitate segmentation of one or more body parts, and wherein information related to a limb movement is determined based on the segmentation of the one or more body parts, and
      determine a sleep disorder diagnosis based on the sound originating from the patient and the movement of the patient,
   wherein the one or more hardware processors are configured to determine (i) a frequency and severity of the limb movement and (ii) a periodic limb movements index corresponding to a number of periodic limb movements per hour of sleep and/or a periodic limb movements arousal index corresponding to a number of arousal-associated periodic limb movements per hour of sleep based on (i) the limb movement and (ii) a sound accompanying the limb movement.

8. The system claim 7, wherein the detector comprises one or more of a visible light detecting camera or an infrared light detecting camera.

9. The system of claim 7, wherein neither the sound sensor nor the movement sensor is in contact with the patient when sound is received or movement is monitored.

10. The system of claim 7, wherein at least one of the sound sensor or the movement sensor is integrated into a housing with the one or more hardware processors.

11. The system of claim 7, wherein the determination of the sleep disorder diagnosis includes a probability indicator for the diagnosis.

12. The system of claim 7, wherein the motion vectors facilitate one or more of a determination of an orientation of the patient, a segmentation of the patient from a bed partner, and an analysis of a local motion.

13. A method for monitoring a sleep session of a patient without making physical contact with the patient, the method comprising:
   generating, with a sound sensor, output signals that convey information related to sound originating from the patient in a sleeping environment;
   projecting, with a light source, a structured light pattern onto the patient which deforms when the patient moves;
   receiving, with a detector, light reflected from the patient;
   generating, with the detector, output signals that convey information related to changes in the structured light pattern projected onto the patient caused by movement of the patient;
   determining, with one or more hardware processors, movement of the patient based on (1) a distance between the light source and the detector, and (2) a change in angle of reflected light from the structured light pattern received from an individual moving point on the patient, wherein images derived from the information related to changes in the structured light pattern are construed wherein an indication of motion vectors is provided, wherein the motion vectors indicate a direction and an amplitude of the movement of the patient, wherein the motion vectors facilitate segmentation of one or more body parts, and wherein information related to a mouth movement is determined based on the segmentation of the one or more body parts;
   determining, with the one or more hardware processors, a sleep disorder diagnosis based on the sound originating from the patient and the movement of the patient in the sleeping environment, and determining, with the one or more hardware processors, parasomnia Bruxism based on the determined mouth movement.

14. The method claim 13, wherein the detector is one or more of a visible light detecting camera or an infrared light detecting camera.

15. The method of claim 13, wherein neither the sound sensor nor the detector is in contact with the patient when sound is received or movement is monitored.

16. The method of claim 13, wherein at least one of the sound input sensor or the detector is integrated into a housing with the one or more hardware processors.

17. The method of claim 13, wherein determining the sleep disorder diagnosis includes determining a probability indicator for the diagnosis.

18. The method of claim 13, wherein the motion vectors facilitate one or more of a determination of an orientation of the patient, a segmentation of the patient from a bed partner, and an analysis of a local motion.

19. A method for monitoring a sleep session of a patient without making physical contact with the patient, the method comprising:
generating, with a sound sensor, output signals that convey information related to sound originating from the patient in a sleeping environment;
projecting, with a light source, a structured light pattern onto the patient which deforms when the patient moves;
receiving, with a detector, light reflected from the patient;
generating, with the detector, output signals that convey information related to changes in the structured light pattern projected onto the patient caused by movement of the patient;
determining, with one or more hardware processors, movement of the patient based on (1) a distance between the light source and the detector, and (2) a change in angle of reflected light from the structured light pattern received from an individual moving point on the patient, wherein images derived from the information related to changes in the structured light pattern are construed wherein an indication of motion vectors is provided, wherein the motion vectors indicate a direction and an amplitude of the movement of the patient, wherein the motion vectors facilitate segmentation of one or more body parts, and wherein information related to a limb movement is determined based on the segmentation of the one or more body parts;
determining, with the one or more hardware processors, a sleep disorder diagnosis based on the sound originating from the patient and the movement of the patient in the sleeping environment; and
determining, with the one or more hardware processors, (i) a frequency and severity of the limb movement and (ii) a periodic limb movements index corresponding to a number of periodic limb movements per hour of sleep and/or a periodic limb movements arousal index corresponding to a number of arousal-associated periodic limb movements per hour of sleep based on (i) the limb movement and (ii) a sound accompanying the limb movement.

20. The method claim 19, wherein the detector is one or more of a visible light detecting camera or an infrared light detecting camera.

21. The method of claim 19, wherein neither the sound sensor nor the detector is in contact with the patient when sound is received or movement is monitored.

22. The method of claim 19, wherein at least one of the sound input sensor or the detector is integrated into a housing with the one or more hardware processors.

23. The method of claim 19, wherein determining the sleep disorder diagnosis includes determining a probability indicator for the diagnosis.

24. The method of claim 19, wherein the motion vectors facilitate one or more of a determination of an orientation of the patient, a segmentation of the patient from a bed partner, and an analysis of a local motion.

25. A system configured to monitor a sleep session of a patient without making physical contact with the patient, the system comprising:
sound input means configured to generate output signals that convey information related to sound originating from the patient in a sleeping environment;
movement detecting means for monitoring movement of the patient in the sleeping environment, the movement means comprising:
a light source configured to project a structured light pattern onto the patient which deforms when the patient moves; and
a detector configured to receive light reflected from the subject, the detector configured to generate output signals that convey information related to changes in the structured light pattern projected onto the patient caused by movement of the patient;
means for receiving and storing data relating to the sound originating from the patient based on the information conveyed by the output signals from the sound input means;
means for determining movement of the patient based on (1) a distance between the light source and the detector, and (2) a change in angle of reflected light from the structured light pattern received from an individual moving point on the patient, wherein images derived from the information related to changes in the structured light pattern are construed wherein an indication of motion vectors is provided, wherein the motion vectors indicate a direction and an amplitude of the movement of the patient, wherein the motion vectors facilitate segmentation of one or more body parts, and wherein information related to a mouth movement is determined based on the segmentation of the one or more body parts; and
means for determining a sleep disorder diagnosis based on the sound originating from the patient and the movement of the patient,
wherein the determination of the sleep disorder diagnosis includes a determination of parasomnia Bruxism based on the determined mouth movement.

26. The system claim 25, wherein the detector comprises one or more of a visible light detecting means or an infrared light detecting means.

27. The system of claim 25, wherein neither the sound input means nor the detector is in contact with the patient when sound is received or movement is monitored.

28. The system of claim 25, wherein at least one of the sound input means or the detector is integrated into a housing with the means for receiving and storing data, means for determining movement of the patient, and/or means for determining the sleep disorder diagnosis.

29. The system of claim 25, wherein the determination of the sleep disorder diagnosis includes a probability indicator for the diagnosis.

30. The system of claim 25, wherein the motion vectors facilitate one or more of a determination of an orientation of the patient, a segmentation of the patient from a bed partner, and an analysis of a local motion.

31. A system configured to monitor a sleep session of a patient without making physical contact with the patient, the system comprising:

sound input means configured to generate output signals that convey information related to sound originating from the patient in a sleeping environment;

movement detecting means for monitoring movement of the patient in the sleeping environment, the movement means comprising:
- a light source configured to project a structured light pattern onto the patient which deforms when the patient moves; and
- a detector configured to receive light reflected from the subject, the detector configured to generate output signals that convey information related to changes in the structured light pattern projected onto the patient caused by movement of the patient;

means for receiving and storing data relating to the sound originating from the patient based on the information conveyed by the output signals from the sound input means;

means for determining movement of the patient based on (1) a distance between the light source and the detector, and (2) a change in angle of reflected light from the structured light pattern received from an individual moving point on the patient, wherein images derived from the information related to changes in the structured light pattern are construed wherein an indication of motion vectors is provided, wherein the motion vectors indicate a direction and an amplitude of the movement of the patient, wherein the motion vectors facilitate segmentation of one or more body parts, and wherein information related to a mouth movement and/or a limb movement is determined based on the segmentation of the one or more body parts; and means for determining a sleep disorder diagnosis based on the sound originating from the patient and the movement of the patient, wherein the determination of the sleep disorder diagnosis includes a determination of (i) a frequency and severity of the limb movement and (ii) a periodic limb movements index corresponding to a number of periodic limb movements per hour of sleep and/or a periodic limb movements arousal index corresponding to a number of arousal-associated periodic limb movements per hour of sleep based on (i) the limb movement and (ii) a sound accompanying the limb movement.

32. The system claim 31, wherein the detector comprises one or more of a visible light detecting means or an infrared light detecting means.

33. The system of claim 31, wherein neither the sound input means nor the detector is in contact with the patient when sound is received or movement is monitored.

34. The system of claim 31, wherein at least one of the sound input means or the detector is integrated into a housing with the means for receiving and storing data, means for determining movement of the patient, and/or means for determining the sleep disorder diagnosis.

35. The system of claim 31, wherein the determination of the sleep disorder diagnosis includes a probability indicator for the diagnosis.

36. The system of claim 31, wherein the motion vectors facilitate one or more of a determination of an orientation of the patient, a segmentation of the patient from a bed partner, and an analysis of a local motion.

* * * * *